(12) United States Patent
Kiesel et al.

(10) Patent No.: US 7,268,868 B2
(45) Date of Patent: Sep. 11, 2007

(54) ANTI-RESONANT WAVEGUIDE SENSORS

(75) Inventors: Peter Kiesel, Palo Alto, CA (US);
Oliver H. Wolst, Walzbachtal (DE);
Michael A. Kneissl, Mountain View, CA (US); H Ben Hsieh, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 229 days.

(21) Appl. No.: 10/976,434

(22) Filed: Oct. 29, 2004

(65) Prior Publication Data
US 2006/0092413 A1 May 4, 2006

(51) Int. Cl.
*G01J 3/44* (2006.01)
*G01J 3/30* (2006.01)
*G01N 21/64* (2006.01)
*G01N 21/65* (2006.01)

(52) U.S. Cl. .................... 356/301; 358/318; 250/458.1

(58) Field of Classification Search ............... 356/318, 356/301; 250/458.1
See application file for complete search history.

(56) References Cited

U.S. PATENT DOCUMENTS

| 5,572,328 | A | 11/1996 | Fouckhardt et al. ........ 356/440 |
| 6,483,959 | B1 | 11/2002 | Sing et al. |
| 6,577,780 | B2 | 6/2003 | Lockhart |
| 6,603,548 | B2 | 8/2003 | Church et al. |

FOREIGN PATENT DOCUMENTS

| EP | 0 679 881 B1 | 11/1995 |
| WO | WO99/44042 | 9/1999 |
| WO | WO 02/25269 A2 * | 3/2002 |

OTHER PUBLICATIONS

Goddard, N., Singh, K., Bounaira, F., Holmes, R., Baldock, S., Pickering, L., Fielden, P., and Snook, R.: Anti-Resosnant Reflecting Optical Waveguides (Arrows) As Optimal Optical Detectors For Microtas Applications, Micro Total Analysis Systems 1998—Proceedings, (1998) 97-100 http://dias.umist.ac.uk/NJG/index.htm.
Goddard, N., Singh, K., Holmes, R., Bounaira, F., Bramwell, C., Mohr, S., Fanning, J. and L., Fielden: Anti-Resonant Reflecting Optical Waveguides (Arrows) Optical Detectors Microsystems, DIAS—UMIST http://dias.umist.ac.uk/NJG/Abstracts/R&D99/index.html.
Singh, K. et al: "Analysis Of Cellular Structure By Light Scattering Measurements In A New Cytometer Design Based on A Liquid-Core Waveguide", IEE Pro.—Nanobiotechnol, vol. 151, No. 1, Feb. 2, 2004, pp. 10-16.
Bernini, R. et al: "Silicon Micromachined Hollow Optical Waveguides For Sensing Applications", IEEE Journal of Selected Topics in Quantum Electronics, IEEE Service Center, vol. 8, No. 1, Jan. 2002, pp. 106-110.

* cited by examiner

*Primary Examiner*—F. L. Evans
(74) *Attorney, Agent, or Firm*—Kent Chen

(57) ABSTRACT

An improved method of analyzing target analytes in a sample is described. The method is based on anti-resonant guided optical waveguides which enables a strongly improved light-target interaction since the light can be guided within the target-containing medium. The light-target interaction can be monitored by many different means to determine characteristics of the target analyte. The anti-resonant waveguide concept is suitable for a large variety of characterization methods and combinations of them, since it is relatively unaffected by changes to both wavelength and film thickness.

39 Claims, 7 Drawing Sheets

| Refractive Index of Analyt n | Angle γ' (degrees) | Angle γ" (degrees) |
|---|---|---|
| 1.00 | 48.2 | – |
| 1.05 | 45.6 | – |
| 1.10 | 42.8 | – |
| 1.15 | 39.9 | 74.4 |
| 1.20 | 36.9 | 64.2 |
| 1.25 | 33.6 | 56.0 |
| 1.30 | 29.9 | 48.4 |
| 1.35 | 25.8 | 40.8 |

ANTI-RESONANT WAVEGUIDE SENSORS

BACKGROUND

The detection of micro-organisms for medical treatments and security systems has taken on increased importance in recent years. Modern medical systems as well as security systems depend on the detection and identification of microorganisms, including bioagents or toxins in the air, food, water, blood or other specimens.

Conventional detection is usually done in the laboratory. Laboratory testing typically uses skilled personnel in a time consuming process. Portable versions of laboratory PCR (polymerase chain reaction) have been developed, however, these devices are bulky and not cost effective.

Optical systems for detecting and identifying microorganisms provide numerous advantages over chemical and other analysis techniques. For example, optical systems can reduce or eliminate the need for field workers to use chemical reactions to detect elements. Optical systems are also often nondestructive to the sample being analyzed.

Most optical biosensor designs rely on interactions between light and a biological sample to provide information on sample characteristics. However, the interaction between light and biological elements in the sample is typically weak. Thus without amplification of the interaction, a large quantity of analyte may be needed. Obtaining such large sample sizes may not be practical for many applications.

In order to increase the interaction between light and biological elements in the sample, optical waveguides may concentrate the intensity of light on the sample. In one use, microorganisms in the sample reside in liquid immediately adjacent to a waveguide surface. Evanescent waves from the waveguide interact with the molecules of the biological elements. However, the interaction between the evanescent waves and the biological elements is still weaker than desired.

Thus an improved system for microorganism detection and identification is needed.

SUMMARY

A method of analyzing a sample is described. The sample includes a medium (e.g., gas, aerosol or fluid) carrying certain target analytes (e.g., toxins, bacteria or their spores), viruses, mammalian or insect cells, parasites, oocytes, or certain chemicals). The method places the sample to be analyzed between a first layer/medium and a second layer/medium. The sample has a sample index of refraction that is less than the indexes of refraction of the first and second layer/medium. A beam of light enters the sample at an angle such that an anti-resonant guided optical waveguide (ARGOW) mode propagates through the sample. Anti-resonance waveguides enable a strongly enhanced interaction between light and analyte. This is useful for many different characterization methods. The interaction between photons in the anti-resonant mode and target analyte (e.g. biological molecules) in the sample is monitored to determine a characteristic of molecules in the sample.

DETAILED DESCRIPTION

An improved sensor that enhances interaction between light and target analytes in a sample is described. Light from a light source is coupled into a sensor chamber, such as a microfluidics channel filled with the sample. By controlling the angle of light entry into the sensor chamber, anti-resonant modes are generated in the sample. The anti-resonant modes allow the sample itself to serve as an optical waveguide resulting in increased interaction between the target molecules and the light.

Figure 1:
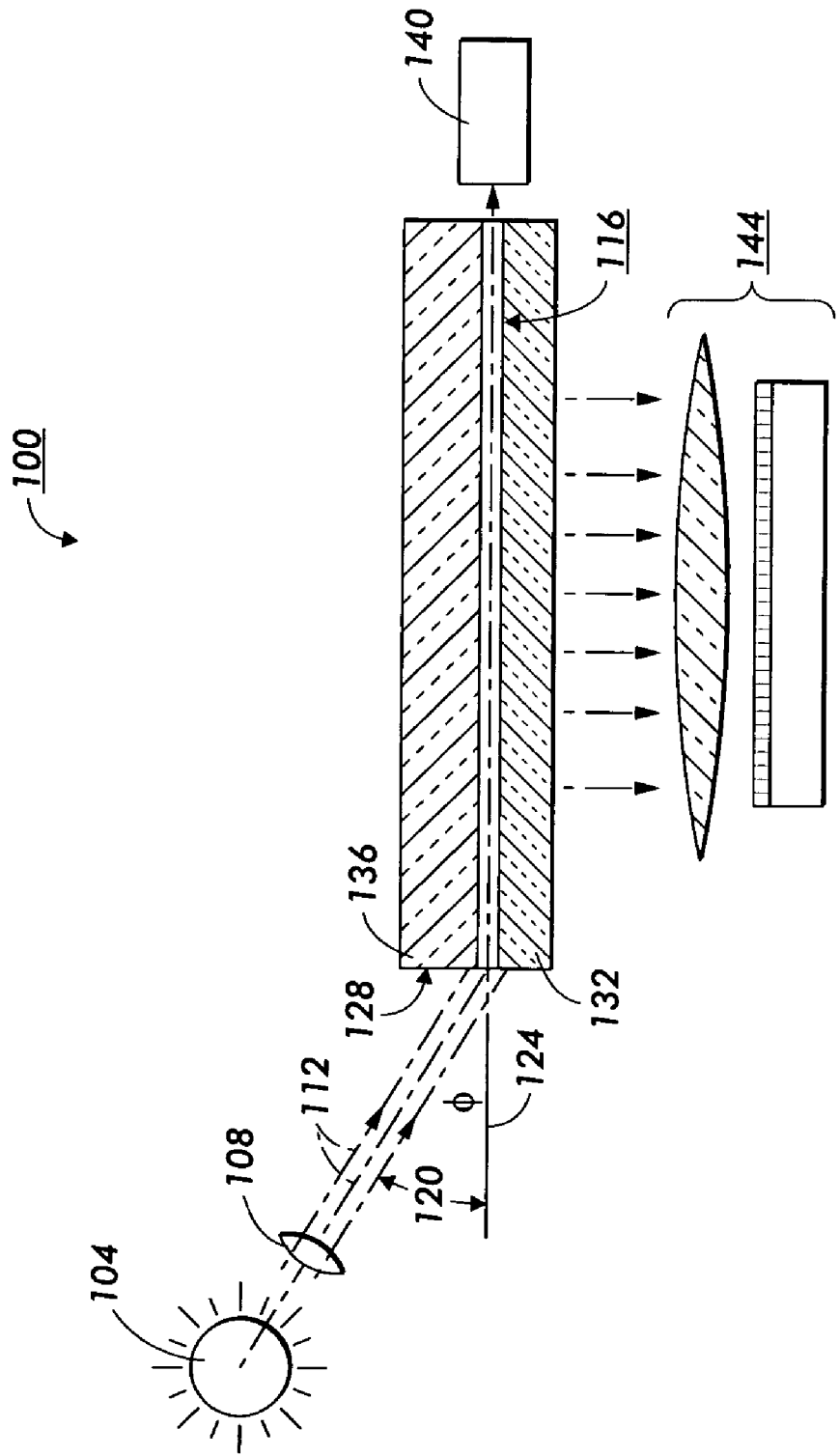
FIG. 1 shows a side sectional overview of an analysis system.

FIG. 1 shows a side view of one embodiment of the optical sensing system 100. In FIG. 1, a light source 104 and/or a lens system 108 directs a light beam 112 into a sample 116. Depending on the test being conducted, light in light beam 112 may be of coherent or incoherent. When coherent light is used, light source 104 is typically a laser. In other cases white light or light emitting diodes may be used.

Light beam 112 enters sample 116 at an angle of incidence 120. As used herein, reference to the word "light", "light beam" and "optical" is should be broadly interpreted to include a broad range of frequencies including ultraviolet, visible, infrared, and far infrared radiation as well as terahertz radiation. As used herein, the angle of incidence is the angle with respect to a normal 124 of the surface 128. The angle of incidence is carefully selected such that an anti-resonant guided optical wave (ARGOW) or mode of light can be set up within sample 116.

Sample 116 is typically a thin film of liquid carrying the target analyte (e.g., biological molecules) to be analyzed. Sample 116 may also be a gas or an aerosol carrying the analyte to be analyzed. If the sample is a gas or aerosol, sealing materials around the perimeter of the chamber containing the sample keeps the gas between substrate 132 and covering layer 136. Sample 116 thickness is usually kept larger than the wavelength of light being used to analyze the sample.

Substrate 132 and covering layer 136 border sample 116 sides. Substrate 132 and covering layer 136 are typically made from a transparent material such as glass. In one embodiment, glass slides are used for substrate 132 and covering layer 136. The index of refraction of the substrate and covering layer are slightly higher than that of the sample 116 to facilitate generation of an anti-resonant wave in sample 116. An example index of refraction of substrate 132 and covering layer 136 might be between 1.4 and 1.8 while the index of refraction of a liquid sample 116 might be between 1.2 and 1.4 although as will be explained, a wide range of other indices are also possible.

The actual conditions used to create an anti-resonant guided optical wave (ARGOW) propagating through a sample sandwiched between two higher index materials may be found by computing the Eigensolutions of the Helmholtz equation for a plane wave propagating along a slab waveguide structure. A general Helmholtz equation for the electric field E is given by:

$$(\nabla^2 + |\vec{k}|^2)E = 0; \quad |\vec{k}| = |\vec{k}_0| \cdot n \quad \text{(Eq. 1)}$$

Assuming a plane wave that propagates along a x-direction within a slab waveguide structure, and confining the wave with respect to the z-orientation results in the following solution to the Helmholtz equation:

$$E = \tilde{E}(z) \cdot e^{i(k_x x - \omega t)}; \quad \frac{\partial E}{\partial y} = 0 \quad \text{(Eq. 2)}$$

where E denotes the electric field, $\tilde{E}(z)$ its z-dependence, $k_x$ the x-component of the wavevector. $\vec{k}_0$ is the lights vacuum wavevector and n the materials refractive index.

In this case the Helmholtz equation reduces to:

$$\left(\frac{\partial^2 E}{\partial z^2} + k_0^2 \cdot n^2(z)\right)\tilde{E}(z) = k_x^2(z) \cdot \tilde{E}(z). \quad \text{(Eq. 3)}$$

The Eigensolutions $\tilde{E}(z)$ can be characterized by $k_x$, or for convenience by a so called effective refractive index $n_{eff}$ defined as:

$$n_{eff} \equiv \frac{k_x}{|\vec{k}_0|} \quad \text{(Eq. 4)}$$

In the previously described slab index guided waveguide structure, the equations above can be numerically solved resulting in a large number of Eigensolutions $\tilde{E}(z)$. These Eigensolutions are called optical modes. Equations 3 and equation 4 also enable computation of the respective refractive indices $n_{eff}$ and modal confinement factors Γ of these modes.

Figure 6:
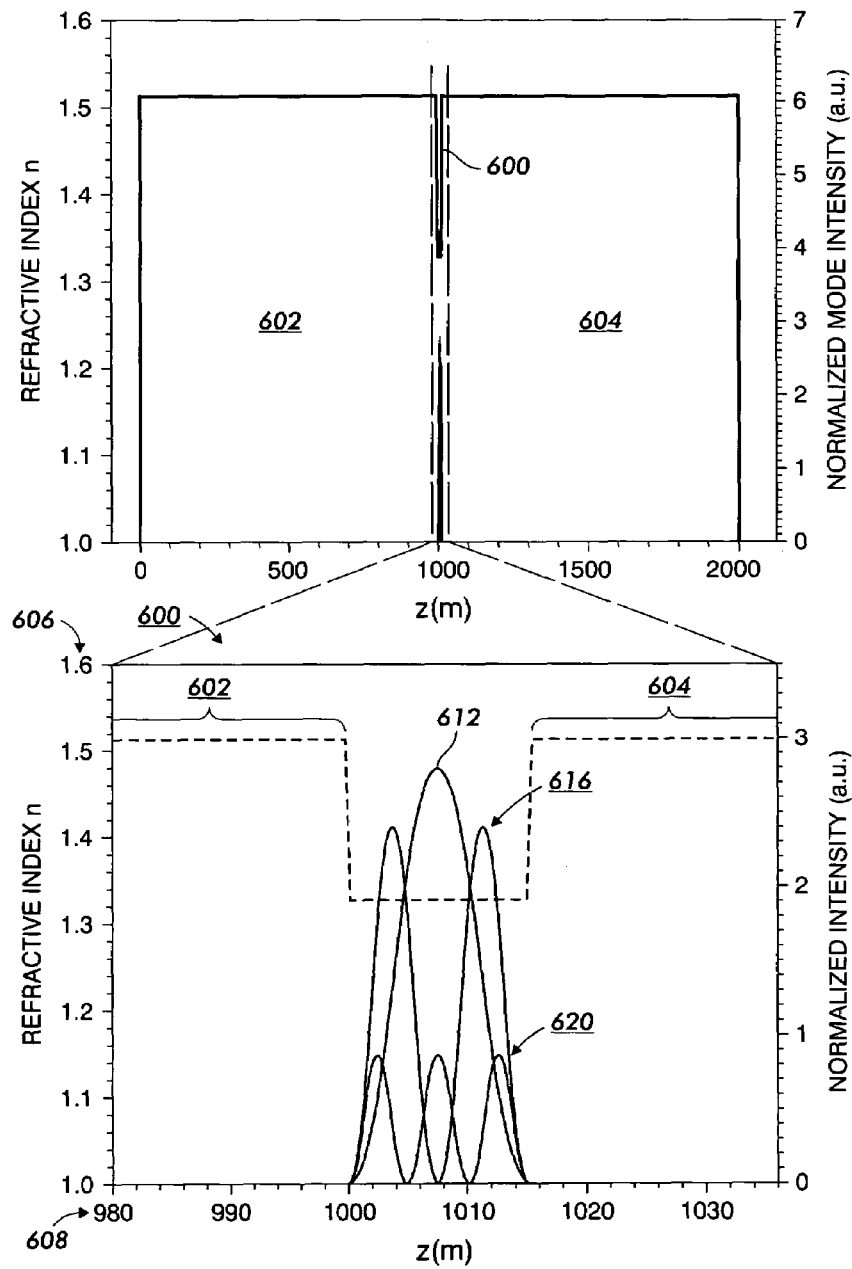
FIG. 6 shows an intensity profile of various anti-resonant modes in an example analyte cross section.

FIG. 6 shows examples of optical modes. In FIG. 6, anti-resonant intensity patterns 612, 616, 620 are plotted across a cross section of a liquid sample 600 placed between glass plates 602, 604. Typical indexes of refraction across the sample are provided along y axis 606. A distance along sample 600 is provided on x axis 608. An example first optical mode is shown by normalized intensity pattern 612, a second optical mode is shown by normalized intensity pattern 616 and a third optical mode is shown by normalized intensity pattern 620.

A confinement factor Γ corresponds to the fraction of the light intensity confined in the waveguide core. For maximum interaction between target molecules in the sample and the light beam, the sample or analyte itself serves as the waveguide core. The core is surrounded by a cladding layer, typically the portion of the medium immediately adjacent to the sample. In future references to the cladding, the "cladding layer" shall refer to a portion of the medium that lies immediately on either side of the sample. The thickness of the cladding layer can be chosen within a wide range but the typical thickness is a several wavelengths of the light propagating in the medium.

In the case of "anti-resonant" waveguides, herein defined to be a waveguide in which the core has a lower refractive index than the cladding layer, a number of optical modes with reasonably large confinement factors, up to and past 90%, can be found. These modes (or Eigensolutions) are characterized by effective refractive indices $n_{eff}$ close to (typically slightly smaller than) the refractive index n of the core layer material. When the core thickness is large compared with the wavelength of propagating light, the $n_{eff}$ of these modes of interest, approaches the refractive index of the core n.

$$d_{core} >> \lambda \Rightarrow n_{eff} \approx n \quad \text{(Eq. 5)}$$

Figures 2, 3:
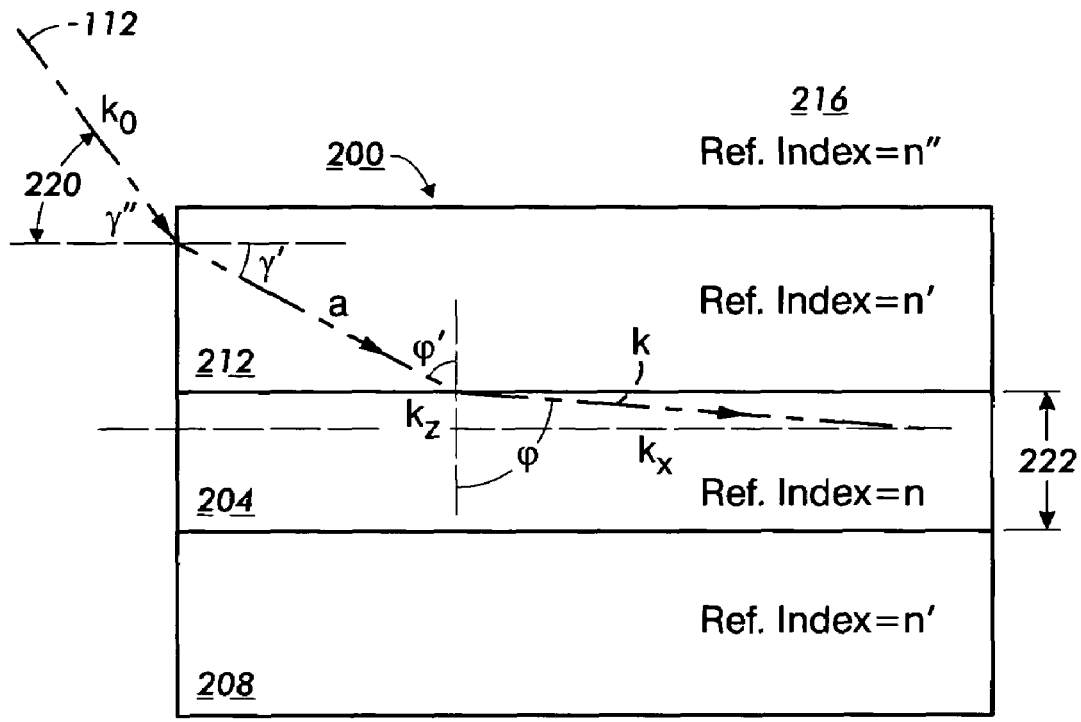
FIG. 2 shows an expanded side sectional view of a waveguide receiving an input light beam with a target-containing sample as a core.
FIG. 3 is a table showing example incidence angles for different analytes surrounded by a glass cladding.

Each Eigenmode can be excited by directing a beam of light at the waveguide at a specific angle of incidence. The angle of incidence corresponds to the effective refractive index $n_{eff}$. FIG. 2 shows one geometry of a slab waveguide 200 where the refractive index of the analyte 204 is n, the refractive index of substrate 208 and cover layer 212 are n' and the refractive index of the surroundings 216 is n". The optimum angle of incidence $\gamma(n_{eff})$ 220 for the structure of FIG. 2 may be derived as follows:

$$\sin(\varphi) = \frac{k_x}{k} = \frac{n_{eff}}{n}; \quad \text{(Eq. 6)}$$

$$\sin(\varphi') = \frac{n}{n'}\sin(\varphi) = \frac{n_{eff}}{n'};$$

$$\cos(\gamma') = \cos(90° - \varphi') = \sin(\varphi');$$

$$\gamma' = \arccos\left(\frac{n_{eff}}{n'}\right);$$

$$\sin\gamma'' = \frac{n'}{n''}\sin\gamma';$$

$$\gamma'' = \arcsin\left(\frac{n'}{n''}\arccos\left(\frac{n_{eff}}{n'}\right)\right);$$

When analyte 204 thickness 220 (typically waveguide core diameter $d_{core} \approx 10 \ldots 100$ μm) is large compared with the wavelength of the incident light ($\lambda = 0.3 \ldots 2$ μm) the approximation of (Eq. 5) is acceptable. Using the equation 4 approximation allows substitution of analyte refractive index n for effective refractive index $n_{eff}$. The substitution results in an angle of incident that depends only on the refractive indices of the analyte, the core layer and the outside world:

$$\gamma'' = \arcsin\left(\frac{n'}{n''}\arccos\left(\frac{n}{n'}\right)\right); \quad \text{(Eq. 7)}$$

An example of a typical set of refractive indices might be an analyte of water with an n=1.34, a glass cladding layer with an n'=1.5 and an air or vacuum surrounding with n"=1. Using a glass cladding in an air surrounding for an example, the table in FIG. 3 lists appropriate angles of incident γ" in order to generate an ARGOW mode based on the sample or analyte refractive indexes.

Figure 4:
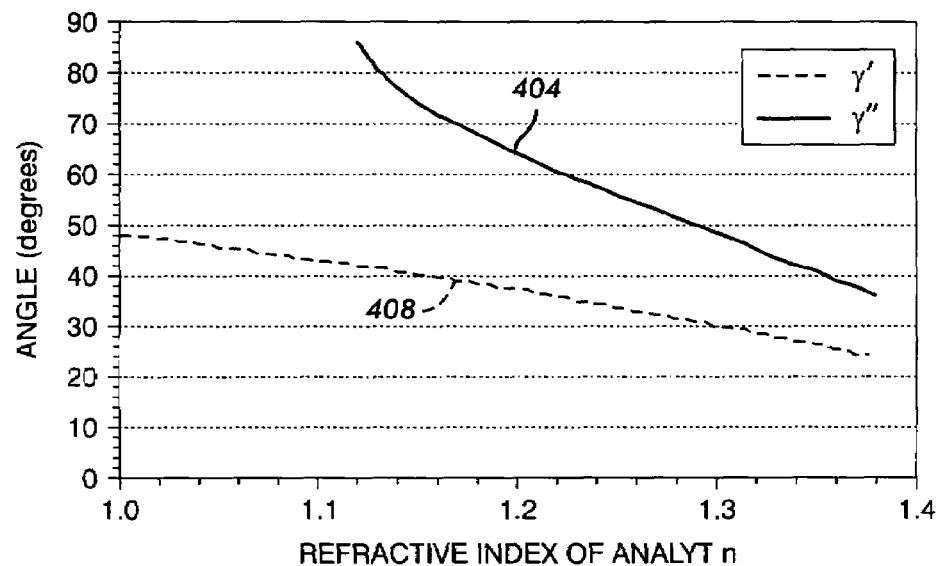
FIG. 4 is a chart that plots an angle of incidence into the waveguide structure of FIG. 2 as a function of the index of refraction of the sample.

FIG. 4 plots the data shown in FIG. 3. As shown in curve 404 of FIG. 4, the angle of incidence increases with decreases in the sample refractive index. At sample refractive indices less than 1.15 (n<1.15), it is very difficult to couple light into the waveguide facette and generate desired anti-resonant modes. Even for n>1.15, the optimum angles for generating anti-resonant modes are still larger than what may be suitable for coupling large amounts of light into the sample. Large angles create difficulties because these angles force the use of smaller diameter beams to hit the facette at the large angles. Furthermore, the use of large angles substantially increases reflection losses.

Figure 5:
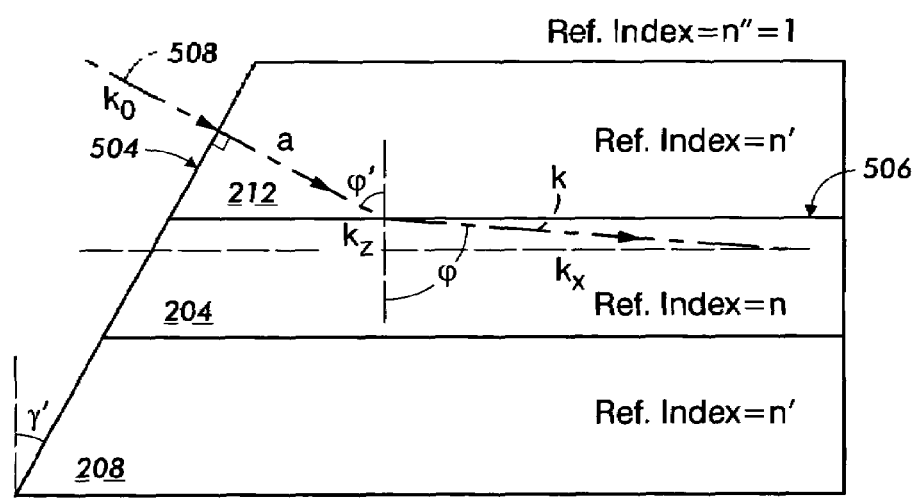
FIG. 5 shows a side sectional view of a waveguide with a biological sample as a core and with a tilted entrance facette.

FIG. 5 shows an alternate structure of FIG. 2 that minimizes losses caused by large incident angles. In FIG. 5, the entrance facette 504 is tilted. Reflections at the facette are minimized when incidence beam 508 perpendicularly enters entrance facette 504. By adjusting the tilt angle γ' such that a beam perpendicularly enters facette 504 and still strikes the cladding and sample interface 506 at an angle Φ' suitable to create an anti-resonant mode, reflections from the facette can be minimized while still generating the desired anti-resonant modes.

Table 3 shows tilt angles γ' for the structure of FIG. 5 that corresponds to various analyte refractive indexes. By tilting the entrance facette 504, generation of anti-resonant optical waves in analytes with refractive indices that range down to n=1 becomes possible. Generating anti-resonant optical waves in low index samples enables the use of gas and aerosol samples. Note that in this case the refractive index of the surrounding medium n" might be chosen smaller than the refractive index of the medium n in order to also allow higher anti-resonant waveguide modes to be guided with reasonable leakage loss.

Although two geometries and end facette designs have been provided in FIG. 2 and FIG. 5, these geometries are provided for example only. It is possible to use other geometries and end facette designs to couple light into an anti-resonant propagating wave. Examples of other geometries include curved end facettes and cylindrical sample shapes rather than the angular end facettes and slab structures described. How to couple light into these other geometries in order to generate an anti-resonant wave in the sample can be determined by solving, either mathematically or numerically the general Helmholtz equation for these geometries. Such calculations are known to those of skill in the art. Thus the scope of the invention should not be limited to the particular example analyzed herein.

Figure 7:
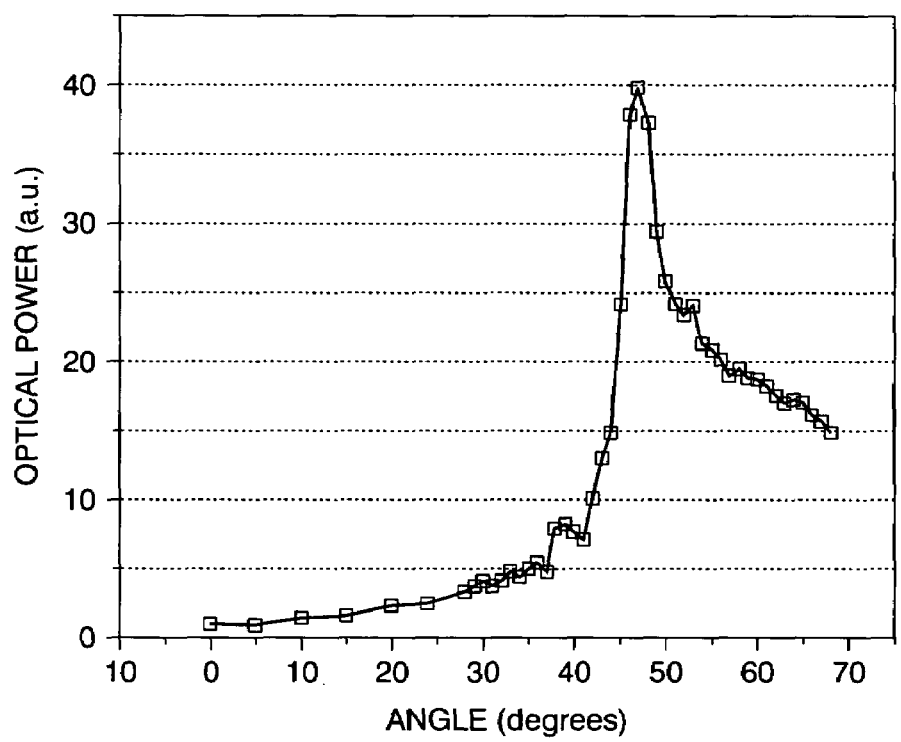
FIG. 7 shows the fluorescence intensity as a function of the coupling angle of the excitation light.

FIG. 7 is a plot of the actual florescent intensity output from a sample as a function of a coupling angle of excitation light into the sample. As will be described, the experimentally generated results of FIG. 7 match closely the theoretical expected coupling efficiencies at various angles of light input.

In order to generate the graph of FIG. 7, excitation light from a single blue high powered LED was coupled at various angles into a side of a liquid film placed between two glass slides. The excitation light excited a fluorescein dye in the liquid film and resulted in fluorescence throughout the entire film area (an area of 25×75 mm$^2$). The resulting fluorescence was then measured.

In the measurements, the measured fluorescence intensity per unit area was similar to that which has been obtained by perpendicularly (from the top) focusing the total excitation power from the LED onto a small spot (e.g. 3×3 mm$^2$) in the sample. The improved fluoresce results from a more efficient use of the excitation light by coupling the light into an ARGOW, in particular, guiding the light between the glass slides. This compares favorably to regular fluorescence detection when the excitation light is input perpendicular to the sample plane and results in transmission of most of the light. Using anti-resonant waveguide excitation the sample itself guides the excitation light between the glass slides providing a long interaction length between light and fluorescent molecules. FIG. 7 plots the fluorescence intensity as a function of the coupling angle of the excitation light. The experimental value for optimum coupling efficiency is in excellent agreement with the theoretically predicted value.

FIG. 6 shows the refractive index profile and the normalized mode intensity of 3 anti-resonant modes of a glass/water/glass anti-resonant waveguide. The anti-resonant modes are calculated assuming 480 nm wavelength light and a 15 μm thick liquid film between two glass slides. The predicted confinement factors for these modes within the liquid film are quite large. For the first three modes confinement factors of Γ=0.9, 0.8 and 0.55 respectively were obtained.

Each mode can be specifically excited by adjusting the incidence angle φ (the angle 120 of FIG. 1). The anti-resonant modes with the highest confinement factors can be excited at a glancing angle φ=46.5°. Glass cladding thickness variations will usually not affect this angle because glass thicknesses are large compared with the wavelength of the propagating light (even if infrared light is used). Changes in liquid film thickness can change the optimum incidence angle; however, calculations show that the effect is very small. Reducing the thickness of the liquid film from 15 μm to 5 μm changes the optimum glancing angle φ from about 46.5° to only about 46.6°. Because within a window of about 0.5 degree, there is available a number of modes with reasonably high confinement factors, the slight change in optimum glancing angle does not present difficulties for the actual system.

Changes in light wavelength also produces slight changes in optimum incidence angle. For example, substituting infrared light (~1500 nm) for blue light (~480 nm) only changes the optimum incidence angle by about 1.8°. The difference in the dispersion of glass and water has a larger influence compared to the different confinement conditions for the different wavelengths which have only small impact on incidence angle.

Figure 8:
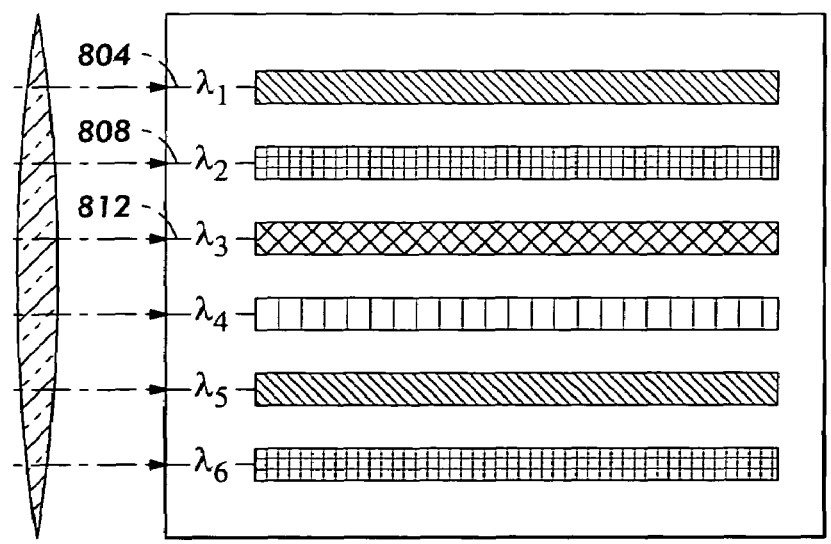
FIG. 8 shows a top view of a system to process in parallel different tests on a sample to determine the presence of a target analyte

The ability of the overall system to accommodate changes in light frequency and sample thickness makes it ideal for use in parallel analytic techniques. These are particularly useful in sophisticated systems where several different tests are to be conducted in parallel to determine the composition or presence of various target analytes. FIG. 8 shows a top view of a sample 800 receiving several frequencies of light 804, 808, 812 at once. Each frequency of light could correspond to a different test to be performed on the sample.

Figure 9:
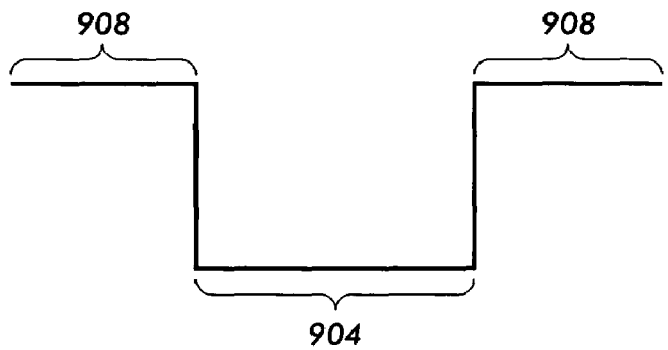
FIGS. 9-14 show sample index profiles of a sample and cladding immediately adjacent the sample.

In the preceding discussion, analysis has been done on step index profiles such as that shown in FIG. 9. However, the generation of ARGOWs should not be limited to such index profiles. FIGS. 9-14 show other index profiles where an index of refraction through the cladding and sample is plotted along a vertical axis and the distance along a cross section of the cladding and sample is plotted along a horizontal axis. As was previously explained, the thickness of the cladding layers is not critical and can be chosen within a wide range. Depending on the application and method of forming the cladding, the thickness of the cladding in one example embodiment is approximately 1 mm (e.g. if glass slides are used). In other cases the cladding may be chosen very thin, not more than three or four wavelengths of the propagating light.

Figure 10:
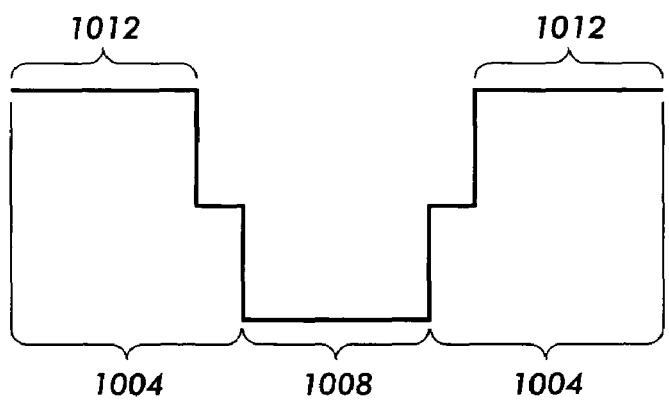

FIG. 10 shows a two step function where cladding region 1004 surrounding sample region 1008. Cladding region 1004 includes two steps in the index of refraction. Systems where a coating is used to prevent sticking of the analyte or other parts of the sample to the sample chamber or medium walls might exhibit such an index of refraction profile. For example, a teflon coating used in cladding region 1004 to coat a glass medium might be a typical example. Teflon has an index of refraction of 1.38 between the glass medium 1012 index of refraction (about 1.44) and a water based sample index of refraction.

Figure 11:
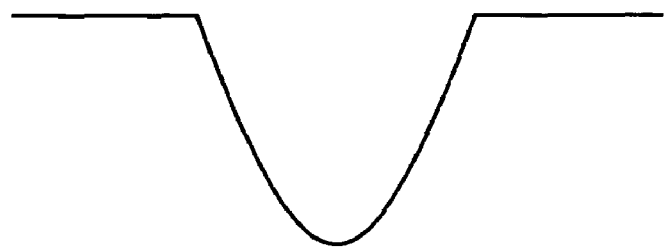
Figure 12:
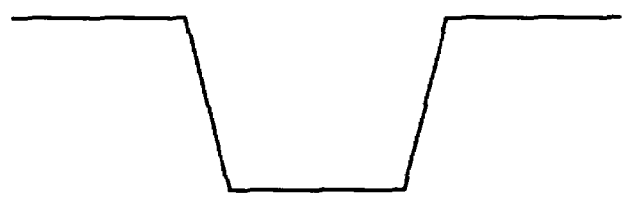
Figure 13:
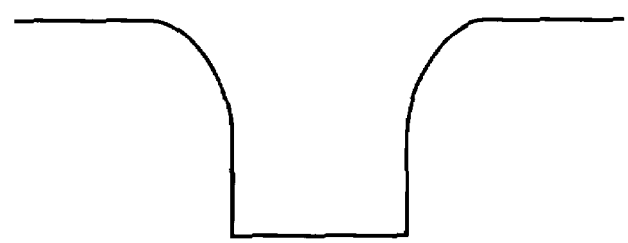
Figure 14:
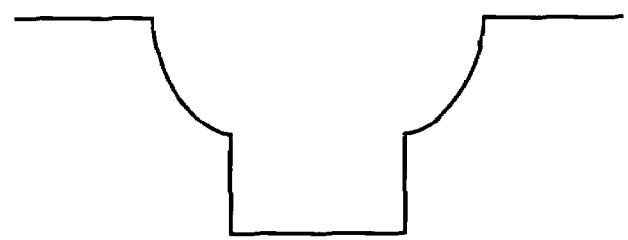

FIG. 11 shows that the sample itself does not have to have a constant index of refraction. FIG. 11 shows a parabolic index of refraction profile that may be exhibited by a fluid sample flowing at different speeds through a medium (e.g. causing phase separation of a mixture). Other monotonically increasing indexes of refraction (monotonically increasing from the edge of the sample through the cladding layer) are shown in FIGS. 12-14. Monotonically increasing indexes of refraction through the cladding region minimizes reflections that may occur from the cladding layers.

Returning to FIG. 1, once an ARGOW propagating wave is generated in the sample, the resulting interaction of the light with the sample contents may be analyzed for information. In one embodiment, a detector 140 of FIG. 1 detects the light that propagates through the sample. In an alternate embodiment, a detector 144 of FIG. 1 detects light that is scattered or refracted by the sample. Depending on the target (e.g. bioagent) to be detected and the particular detection technique to be used, detectors 140, 144 may include wavelength sensitive elements such as gratings, prisms, Bragg reflectors or resonators.

Wavelength sensitive elements enable identification of signatures and specific biological or chemical agents. Detectors 140, 144 may also integrate the wavelength sensitive elements with conventional optics or micro-optics components including mirrors and lenses. In some embodiments, the detectors may include a means for converting the optical signal to an electrical signal. Such conversions may be achieved using a charge coupled device, a photosensor, or any of a variety of conversion devices. Once converted to an electrical signal, detector 140, 144 output can be analyzed using electric processors, such as microprocessors (not shown).

Detector 140 of FIG. 1 detects light transmitted by sample 116. In one embodiment, the light transmitted by sample 116 is analyzed by processors coupled to the detector to determine the presence or absence of chemical, environmental or biological molecules in sample 116. The output of detector 140 may also be used to analyze the characteristics of molecules in sample 116. An example of using detectors to detect light transmitted by a sample and a processor to analyze the detector output is provided in U.S. Pat. No. 6,603,548 entitled "Biosensor" by Church et al. which is hereby incorporated by reference in its entirety.

In an alternate embodiment, instead of detecting light that is transmitted, a second detection system such as detector array 144 may detect light that is scattered or otherwise output by sample 116. Scattered light may be caused by reflection or refraction of light by molecules in sample 116. Example scattering techniques include elastic and inelastic light scattering spectroscopy as described in Introduction to Biophotonics, by Paras N. Prasad ISBN 0-471-28770-9, Wiley-Interscience 2003) which is hereby incorporated by reference in its entirety.

In still another embodiment, light output from sample 116 may be caused by fluorescence that results from binding of chemical elements in the sample to biological materials. The binding results in fluorescence when an excitation source, such as the anti-resonant light propagating in the sample is present. U.S. Pat. No. 6,577,780 by Lockhart entitled Cell Designs for Optical Sensors describes using antigens that attach to antibodies resulting in a structure that fluoresces in the presence of an evanescent field. U.S. Pat. No. 6,577,780 by Lockhart is hereby incorporated by reference in its entirety. By using anti-resonant waves propagating through the sample instead of evanescent fields, the sensitivity of the system can be improved.

Besides the examples given, many other optical detection and sensing techniques may be used with sensors 140 and 144. Those techniques include, but are not limited to single or multi-color light-induced intrinsic fluorescence or fluorescence from tagged molecules and applications derived from the manipulation of the fluorescent lights such as fluorescence lifetime imaging microscopy (FLIM), fluorescence resonance energy transfer (FRET), fluorescence correlation spectroscopy (FCS), etc., light scattering or vibrational spectroscopy (Raman, IR) or spectroscopic applications utilizing optical activity of chiral media such as circular dichroism (CD), among others. A more detailed description of various detection techniques utilizing photon interactions is provided in Chapter 4 of "*Introduction to Biophotonics*" by Paras N. Prasad, ISBN 0-471-28770-9, Wiley-Interscience 2003) which is hereby incorporated by reference.

Although optical detection techniques have been described, other methods of detecting the enhanced light-target interaction may be used. For example thermal detection techniques may be used. Predetermined light wavelengths may initiate a specific exothermic or endothermic chemical reaction which causes a temperature change. The detected temperature change indicates the presence of the reaction and thus the presence of compounds needed to create the reaction. Other example detection techniques include, but are not limited to, ARGOW induced photo ionization or photo fractionation. The photo ionization or photo fractionation generates charged particle which can be detected by known means such as a Coulter Counter.

In order to speed up analysis of the samples, parallel processing of a sample may occur. Thus the techniques described are not mutually exclusive and may be used in conjunction or in parallel to yield rapid detailed analysis of molecules in the sample.

A number of example geometries for a sample geometry and analysis techniques have been provided. However, the details provided have been provided as examples to facilitate understanding of the invention, and to provide sample calculations. However, the scope of the invention should not be limited to these geometries nor the particular analysis techniques described. Instead, the invention should only be limited by the claims, as originally presented and as they may be amended to encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. A method of analyzing a sample containing a target analyte, the method comprising:

arranging the sample between a first medium and a second medium, the sample having a sample index of refraction, the sample index of refraction less than an index of retraction of the first medium, the sample index of refraction also less than an index of refraction of the second medium;

directing a beam of light into the sample through a tilted entrance end facet at a first end of the first or second medium, the beam of light entering the tilted entrance facet at an angle such that an anti-resonant guided optical wave (ARGOW) propagates through the sample; and, detecting the interaction between the light in the anti-resonant guided wave and the target analyte in the sample.

2. A method of analyzing a sample containing a target analyte, the method comprising:
arranging the sample between a first medium and a second medium, the sample having a sample index of refraction, the sample index of refraction less than an index of refraction of the first medium, the sample index of refraction also less than an index of refraction of the second medium;
directing a beam of light into the sample wherein the beam of light is focused prior to entering an entrance facet, such that multiple anti-resonant guided optical waveguide modes propagate through the sample; and,
detecting the interaction between the light in the anti-resonant guided wave and the target analyte in the sample.

3. The method of claim 1 wherein the sample includes at least one marker molecule that attaches to the target analyte and causes fluorescence light when exposed to light.

4. The method of claim 1 wherein the detecting operation uses native intrinsic fluorescence of the analytes, the native intrinsic fluorescence stimulated by incident lights.

5. The method of claim 1 wherein the detecting operation uses light scattering.

6. The method of claim 5 wherein the light scattering is elastic.

7. The method of claim 5 wherein the light scattering is inelastic.

8. The method of claim 5 wherein the light scattering is Raman spectroscopy.

9. The method of claim 1 wherein the detecting operation utilizes the optical activity of chiral media included in the sample.

10. The method of claim 1 wherein the light in the beam of light is coherent.

11. The method of claim 1 wherein the beam of light is generated by a laser.

12. The method of claim 1 wherein the first medium is glass.

13. The method of claim 1 wherein the first medium is made of polymer materials.

14. The method of claim 12 wherein the second medium is glass.

15. The method of claim 13 wherein the second medium is made of polymer materials.

16. The method of claim 1 wherein the sample is a liquid that carries the target analyte, the liquid serving as a waveguide.

17. The method of claim 1 wherein the target analyte is immobilized on a surface of the first medium, the target analyte embedded in a solution.

18. The method of claim 1 wherein the solution is one of a fixation solution, an antifade solution and a staining solution.

19. The method of claim 1 wherein the sample is a gas that carries the target analyte.

20. The method of claim 1 wherein the sample is an aerosol that carries the target analyte.

21. The method of claim 1 wherein the sample is a flowing stream of analyte-containing liquid inside a capillary tube.

22. The method of claim 1 wherein the sample has an index of refraction less than 1.4.

23. The method of claim 1 wherein the sample has an index of refraction less than 1.15.

24. The method of claim 1 wherein the first medium and the second medium have the same index of refraction.

25. A method of analyzing a sample containing a target analyte, the method comprising:
arranging the sample between a first medium and a second medium, the first medium includes a first cladding region immediately adjacent to the sample and the second medium includes a second cladding region immediately adjacent to the sample, the first cladding region having a varying index of refraction, the sample having a sample index of refraction, the sample index of refraction less than an index of refraction of the first medium, the sample index of refraction also less than an index of refraction of the second medium;
directing a beam of light into the sample at an angle such that an anti-resonant guided optical wave (ARGOW) propagates through the sample; and,
detecting the interaction between the light in the anti-resonant guided wave and the target analyte in the sample.

26. The method of claim 25 wherein the beam of light has a wavelength, the first cladding region having an index of refraction that monotonically increases with distance for a distance of two wavelengths from an interface between the sample and the first medium.

27. The method of claim 26 wherein the monotonic increases include regions where the index of refraction does not change.

28. The method of claim 1 wherein the anti-resonant guided optical wave is a solution of the Helmholtz equation.

29. A system to analyze a sample comprising:
a sample including a target analyte, the sample having a first index of refraction;
a top layer and a substrate surrounding the sample, one of the top layer or the substrate having a tilted end facet for receiving light, the top layer having a second index of refraction and the substrate having a third index of refraction, the second index of refraction and the third index of refraction both greater than the first index of refraction; and,
a light source to direct light into the sample via the tilted end facet and generate an anti-resonant guided optical mode in the sample; and,
an analyzing system to detect the interaction of the light propagating in the sample with the target analyte.

30. The system of claim 29 wherein the second index of refraction is equal to the third index of refraction.

31. The system of claim 29 wherein the sample is a liquid.

32. The system of claim 29 wherein the sample is a gas.

33. The system of claim 29 wherein the analyzing system is a detector that detects the light absorbed by the sample.

34. The system of claim 29 wherein the analyzing system is a detector that detects the light scattered by the sample.

35. A system to analyze a sample comprising:
a sample including a target analyte, the sample having a first index of refraction;
a top layer and a substrate surrounding the sample, the top layer having a second index of refraction, the top layer includes a top layer cladding region immediately adjacent to the sample, the top layer cladding region has an index of retraction that varies and the substrate having a third index of refraction, the second index of refraction and the third index of refraction both greater than the first index of refraction; and,
a light source to direct light into the sample and generate an anti-resonant guided optical mode in the sample; and, an analyzing system to detect the interaction of the light propagating in the sample with the target analyte.

36. The system of claim 35 wherein the index of refraction in the top layer cladding region monotonically increases with increasing distance from the top layer cladding region and sample interface for a distance of at least two wavelengths of light in the anti-resonant guided optical mode.

37. The system of claim 29 wherein the substrate includes a substrate cladding region immediately adjacent to the sample, the substrate cladding region has an index of refraction that varies.

38. The system of claim 37 wherein the index of refraction in the substrate cladding region monotonically increases with increasing distance from the substrate region and sample interface for a distance of at least two wavelengths of light in the anti-resonant guided optical mode.

39. The system of claim 29 wherein the light in the anti-resonant guided optical mode is a solution to the Helmholtz equation.

* * * * *